United States Patent
Taylor et al.

(10) Patent No.: US 7,210,966 B2
(45) Date of Patent: May 1, 2007

(54) MULTI-POLAR FEEDTHROUGH ARRAY FOR ANALOG COMMUNICATION WITH IMPLANTABLE MEDICAL DEVICE CIRCUITRY

(75) Inventors: William J. Taylor, Anoka, MN (US); Shawn D. Knowles, St. Francis, MN (US); John C. Olson, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 275 days.

(21) Appl. No.: 10/889,771

(22) Filed: Jul. 12, 2004

(65) Prior Publication Data

US 2006/0009813 A1    Jan. 12, 2006

(51) Int. Cl.
*H01R 13/66* (2006.01)
(52) U.S. Cl. .................. 439/620.09; 439/587; 361/302
(58) Field of Classification Search ........... 439/620.09, 439/620.05, 620.07, 620.13, 587, 271, 278; 361/302, 307, 301.1, 323; 607/2, 5
See application file for complete search history.

(56) References Cited

U.S. PATENT DOCUMENTS

| | | | |
|---|---|---|---|
| 4,991,582 A * | 2/1991 | Byers et al. ................... | 607/2 |
| 5,287,076 A | 2/1994 | Johnescu et al. | |
| 5,333,095 A | 7/1994 | Stevenson et al. | |
| 5,470,345 A | 11/1995 | Hassler et al. | |
| 5,650,759 A | 7/1997 | Hittman et al. | |
| 5,735,884 A | 4/1998 | Thompson et al. | |
| 5,759,197 A | 6/1998 | Sawchuk et al. | |
| 5,782,891 A | 7/1998 | Hassler et al. | |
| 5,836,992 A | 11/1998 | Thompson et al. | |
| 5,866,851 A | 2/1999 | Taylor et al. | |
| 5,867,361 A | 2/1999 | Wolf et al. | |
| 5,870,272 A | 2/1999 | Seifried et al. | |
| 5,896,267 A | 4/1999 | Hittman et al. | |
| 5,905,627 A | 5/1999 | Brendel et al. | |
| 5,959,859 A | 9/1999 | Stevenson et al. | |
| 5,999,399 A | 12/1999 | Maki et al. | |
| 6,349,025 B1 * | 2/2002 | Fraley et al. ................ | 361/302 |
| 6,414,839 B1 | 7/2002 | Wolf et al. | |
| 6,660,116 B2 * | 12/2003 | Wolf et al. .................. | 361/302 |
| 6,765,780 B2 * | 7/2004 | Brendel et al. ............. | 361/302 |

* cited by examiner

*Primary Examiner*—Felix O. Figueroa
(74) *Attorney, Agent, or Firm*—Paul H. McDowall; Girma Wolde-Michael

(57) ABSTRACT

An improved multi-polar feedthrough assembly employs a particular metallic ferrule material for improved dimensional stability during initial fabrication and sustained hermetic operation. In one aspect, the disclosure relates to implantable medical devices (IMDs) including an IMD enclosure fabricated with grade 2 titanium and having a ferrule material fabricated with grade 4 titanium or grade 5 titanium. In one form, the multi-polar feedthrough assembly includes a filtered feedthrough array (e.g., employing capacitive filters coupled to the electrically conductive pins or serpentine conductors of the array). According to another aspect, the improved multi-polar feedthrough assembly incorporates additional pins, thus increasing the footprint of the assembly, and the additional pins provide analog electrical communication between operative circuitry inside an IMD and analog components external to the IMD.

13 Claims, 8 Drawing Sheets

| Ferrule Feature | Mean Grade 2 | Sdev Grade 2 | Mean Grade 4 | Sdev Grade 4 | Mean Grade 5 | Sdev Grade 5 | Feedthrough Design Impact |
|---|---|---|---|---|---|---|---|
| Height Straightness | 0.0045 | 0.00209 | 0.0026 | 0.0064 | 0.0007 | 0.00025 | Shield Laser Welding |
| Width Straightness | 0.0020 | 0.00106 | 0.0010 | 0.0002 | 0.0003 | 0.00010 | Shield Laser Welding |
| Capacitor Cavity Edge Straightness | 0.0055 | 0.000242 | 0.0042 | 0.00145 | 0.0007 | 0.00057 | EMA Attachment & EMI Filter Capacitor Containment |
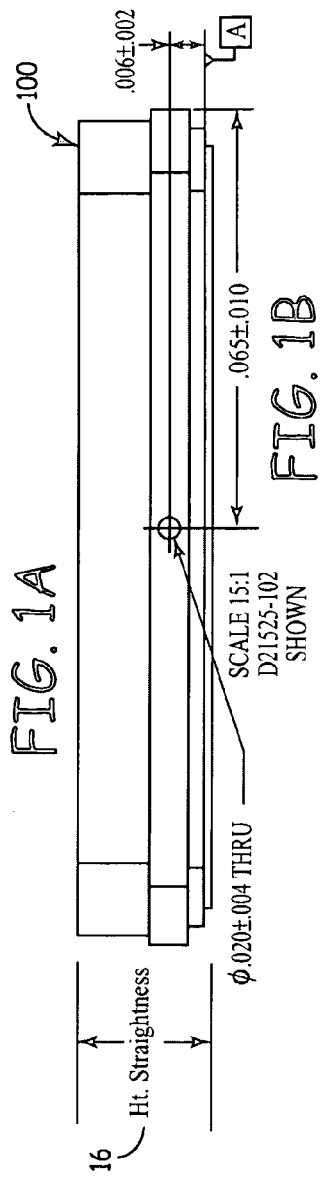
FIG. 1A
FIG. 1B
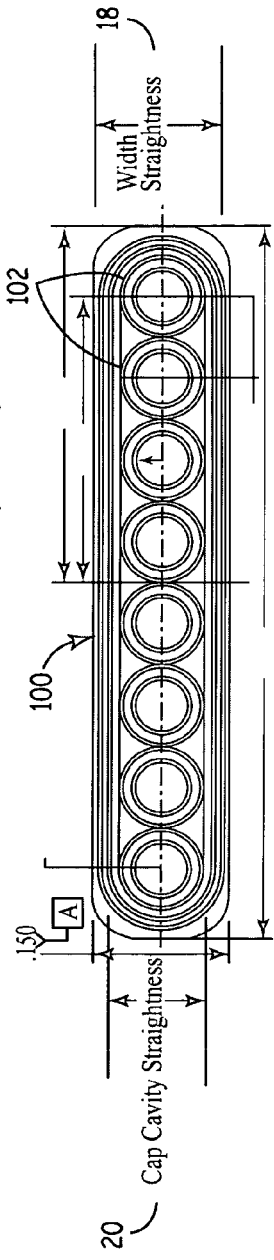
FIG. 1C

SECTION A-A

MULTI-POLAR FEEDTHROUGH ARRAY FOR ANALOG COMMUNICATION WITH IMPLANTABLE MEDICAL DEVICE CIRCUITRY

FIELD OF THE INVENTION

The present invention relates to electrical communication of signals through a conductive substrate; for example, a titanium shell of a hermetically sealed implantable medical device.

BACKGROUND OF THE INVENTION

Electrical feedthroughs serve the purpose of providing an electrical circuit path extending from the interior of a hermetically sealed enclosure or housing to an external point outside the enclosure. Implantable medical devices (IMDs) such as implantable pulse generators (IPGs) for cardiac pacemakers, implantable cardioverter defibrillators (ICDs), nerve, brain, organ and muscle stimulators and implantable gastric monitors, or the like, employ such electrical feedthroughs through a hermetically-sealed enclosure that surrounds operative internal circuitry and electrically couples said circuitry with external medical electrical leads and associated electrodes.

Such feedthroughs typically include a ferrule adapted to fit within an opening in the enclosure, one or more conductor and a non-conductive hermetic glass or ceramic seal which supports and electrically isolates each such conductor from the other conductors passing through it and from the ferrule. The IMD enclosure is formed of a biocompatible metal such as titanium, although non-conductive ceramic materials have been proposed for forming the enclosure. The ferrule is typically of a metal that can be welded or otherwise mechanically coupled to the enclosure in a hermetically sealed manner.

Initially, single pin feedthroughs supported by glass, sapphire and ceramic were used with hermetically sealed IPGs. As time has passed, the volume and, consequently the surface area, of enclosures for IMDs has dramatically decreased and the number of medical electrical leads and associated electrodes coupled with the internal circuitry of an IMD has increased. Consequently, use of the relatively large single pin feedthroughs was no longer feasible, and numerous multiple conductor feedthroughs have been used or proposed for use that fit within the smaller sized opening and provide two, three, four or more conductors. Examples include those depicted and described in U.S. Pat. Nos. 6,660,116; 6,414,835; and 5,870,272 the contents of which are hereby incorporated herein by reference.

Many different insulator structures and conductor structures are known in the art of multiple conductor feedthroughs wherein the insulator structure also provides a hermetic seal to prevent entry of body fluids through the feedthrough and into the housing of the medical device. The conductors typically comprise electrical wires or pins that extend through a glass and/or ceramic layer within a metal ferrule opening as shown, for example, in commonly assigned U.S. Pat. Nos. 4,991,582; 5,782,891; and 5,866,851 or through a ceramic enclosure as shown in the commonly assigned '891 patent and in U.S. Pat. No. 5,470,345.

Such multi-conductor feedthroughs have an internally disposed portion configured to be disposed inside the enclosure for connection with electrical circuitry and an externally disposed portion configured to be disposed outside the enclosure that is typically coupled electrically with connector elements for making connection with the leads, electrodes or sensors. The elongated lead conductors extending from the connector elements effectively act as antennae that tend to collect stray electromagnetic interference (EMI) signals that may interfere with normal IMD operations. At certain frequencies, for example, EMI can be mistaken for programming signals from an external programming device that can then cause an IMD to change operating mode.

This problem has been addressed in certain of the above-referenced patents by incorporating a capacitor structure upon the internally facing portion of the feedthrough ferrule coupled between each feedthrough conductor and a common ground, the ferrule, to filter out any high frequency EMI transmitted from the external lead conductor through the feedthrough conductor. The feedthrough capacitors originally were discrete capacitors but presently can take the form of chip capacitors that are mounted as shown in the above-referenced '891, '435, '476, and '906 patents and in further U.S. Pat. Nos. 5,650,759; 5,896,267; and 5,959,829, for example. Or, the feedthrough capacitors can take the form of discrete discoidal capacitive filters or discoidal capacitive filter arrays as shown in commonly assigned U.S. Pat. Nos. 5,735,884; 5,759,197; 5,836,992; 5,867,361; and 5,870,272 and further U.S. Pat. Nos. 5,287,076; 5,333,095; 5,905,627 and 5,999,398. These patents disclose use of discoidal filters and filter arrays in association with conductive pins which are of relatively large scale and difficult to miniaturize without complicating manufacture. It is desirable to further miniaturize and simplify the fabrication of the multi-conductor feedthrough assembly.

A high integrity hermetic seal for medical implant applications is very critical to prevent the ingress of body fluids into the IMD. Even a small leak rate of such body fluid penetration can, over a period of many years, build up and damage sensitive internal electronic components. This can cause catastrophic failure of an IMD. The ferrule of a feedthrough for an IMD typically is selected from a material having physical properties that match the properties of the surrounding IMD enclosure. For example, if an IMD enclosure is constructed from grade 2 titanium, a feedthrough ferrule of grade 2 titanium is implemented. However, as the dimensions of such prior art feedthroughs have expanded, combined with the high temperature they are typically subjected to during fabrication the inventors found that the grade 2 titanium oftentimes fails to maintain the close dimensional tolerance required to guarantee long-term hermeticity. That is, the grade 2 titanium metal component of the ferrule changes shape which potentially undermines the close fit of the ferrule in the corresponding aperture of the enclosure thereby negatively effecting the ability to repeatably join the feedthrough to the enclosure via welding. Furthermore, the inventors posit that when subjected to high temperature brazing to seal the interface between a ferrule and an insulator member such relatively high-grade titanium undergoes random dimensional distortion. This random distortion can depend upon such factors as the manner of fabrication of the high grade titanium (e.g., how it was initially forged, drawn into sheet form, etc.) and thus is essentially unpredictable. Furthermore, the inventors suggest that at least part of the reason that grade 2 titanium distorts relates to the physical composition thereof. That is, grade 2 titanium comprises relatively small sized grains and when heated up to or in excess of the phase transition temperature (approximately 850 degrees Celsius) the coupling between the grade 2 titanium grains changes and such changes can lead to a loss of the originally specified dimensions of grade 2 titanium components. The phase transition temperature increases with increasing impurity content, (e.g., grade 4 has a transition temperature of approximately 950 degrees Celsius).

Thus, the inventors have recognized a need in the art to fabricate highly accurately dimensioned components that are integral to high-grade titanium IMD enclosures so that long-term hermeticity is maintained. In particular, the inventors have discovered that as the overall surface area of diverse IMDs has decreased relative to the size of certain integral IMD-surface components (e.g., multi-polar feedthrough assemblies), maintaining dimensional is critical to maintaining long-term hermeticity and to the ability to mount accessories directly to the feedthrough, such as, but not limited to modules for electronic assembly or multi-hole EMI filter capacitors contained in a single dielectric structure. In addition, the inventors has discovered that, in addition to the potential negative impact to long-term fit issue with the enclosure & with components added to the feedthrough, the traditional grade-matching (i.e., grade 2 titanium enclosure and grade 2 titanium ferrule) reduces manufacturing yield of acceptable feedthrough (and ferrule) components and finally assembled IMDs.

Moreover, highly accurately dimensioned ferrules lead to robust feedthrough arrays of simplified construction, utilizing straightforward and uncomplicated assembly, thus resulting in overall manufacturing cost reductions. The inventors contemplate applying the present invention to myriad multi-polar feedthrough assemblies, including those designed for effectively filtering out undesirable EMI. The present invention fulfills these needs and provides other related advantages which will be appreciated by those skilled in the art as defined by the appended claims.

SUMMARY OF THE INVENTION

As noted hereinabove, electrical feedthroughs beneficially provide electrical communication between internal operative circuitry to electrical components external to an IMD. However, as the number of discrete conductive feedthrough pins and the size of feedthrough arrays has increased while the available surface area has decreased previously acceptable dimensional instability of the array has been discovered to cause loss of hermeticity and thus, reduce IMD manufacturing yields.

According to one aspect of the invention, an improved multi-polar feedthrough array employs a particular metallic ferrule material for improved dimensional stability during initial fabrication and sustained hermetic operation. According to the invention, the IMD enclosure consists of grade 2 titanium and the ferrule material comprises grade 4 titanium or grade 5 titanium.

In one form of the invention, the multi-polar feedthrough assembly comprises a filtered feedthrough array (e.g., employing capacitive filters coupled to the electrically conductive pins or serpentine conductors of the array).

According to another aspect of the invention, the improved multi-polar feedthrough array incorporates additional pins, thus further increasing the footprint of the array, and the additional pins provide analog and/or digital electrical communication between operative circuitry inside an IMD and analog and/or digital components external to the IMD. Capacitors attached to a feedthrough (either surface or internally mounted) are generally well known for filtering stray electromagnetic interference (EMI) signals that are randomly impinging upon the external electrical components and IMD enclosure so the EMI cannot affect internal circuitry of the IMD. However, such capacitive filter feedthrough arrays would also filter or modify desirable analog electrical signals such as those emanating from chronically implanted sensors disposed on, about or spaced from an IMD. Such signals include near—and long-range radio-frequency (RF) communication signals and physiologic sensor signals (e.g., signals related to venous or arterial pressure, temperature, acceleration, flow, body fluid pH, glucose, metabolites and the like).

According to this aspect of the invention, in part to reduce the number of hermetically-sealed sites, one or more conductive feedthrough pins are added to a multi-polar feedthrough array to accommodate such sensor signals and/or RF communication signals, and the like. However, the RF signals and sensor signals require very low signal noise, therefore the capacitor structure most be eliminated or modified to minimize stray capacitance which would degrade such analog and/or digital signals. Grouping the feedthrough pins according to this form of the invention results in getting a larger number of signals through the enclosure substrate in a smaller area, which in turn makes it easier to build the feedthrough and incorporate the feedthrough into the enclosure. Thus, the family of multi-polar feedthrough arrays provided pursuant to the present invention provides RF antenna and/or sensor capability in a reduced volume package. According to the invention, any capacitors (either surface—or internally-mounted) previously attached to an analog and/or digital telemetry-antenna circuit or analog and/or digital sensor for filtering stray EMI signals is removed or eliminated. Alternatively, one or more feedthrough pins are added to the multi-polar feedthrough array void of any filtering circuitry. Thus, since the RF antennas and sensor signals require very low signal noise, the capacitor structure must be modified to minimize stray capacitance, which would degrade the signals.

The incorporation of additional functionality (i.e. antenna and sensing capability) to the feedthrough ultimately saves device volume, thereby reducing overall device volume. The invention also provides a FT with variable EMI filtering based upon the FT wire need(s) (i.e. for RF antenna performance, low capacitance and stray inductance are required). In one aspect of this embodiment, one or more spacer members mechanically supports the unfiltered feedthrough pin(s). In another aspect, the unfiltered feedthrough pin(s) are spaced from the capacitive elements to avoid fringing fields and so-called edge effects of the capacitive elements.

The following drawings are not drawn to scale and common reference numerals are utilized to refer to like elements throughout the written description. Of course, the invention is not limited to the illustrate embodiments but rather only by the appended claims which define the literal metes and bounds of the claims, and equivalents thereof.

BRIEF DESCRIPTION OF THE DRAWINGS

FIG. 1A set forth a table of empirical dimensional data for several grades of titanium ferrules, FIG. 1B depicts an elevational side view of an eight-hole ferrule that illustrates the "height straightness" dimension, and FIG. 1C depicts a plan view of the eight-hole ferrule of FIG. 1B illustrating the "width straightness" and "cap cavity straightness" dimensions set forth in the table of FIG. 1A.

DETAILED DESCRIPTION OF THE ILLUSTRATED EMBODIMENTS

Figure 2:
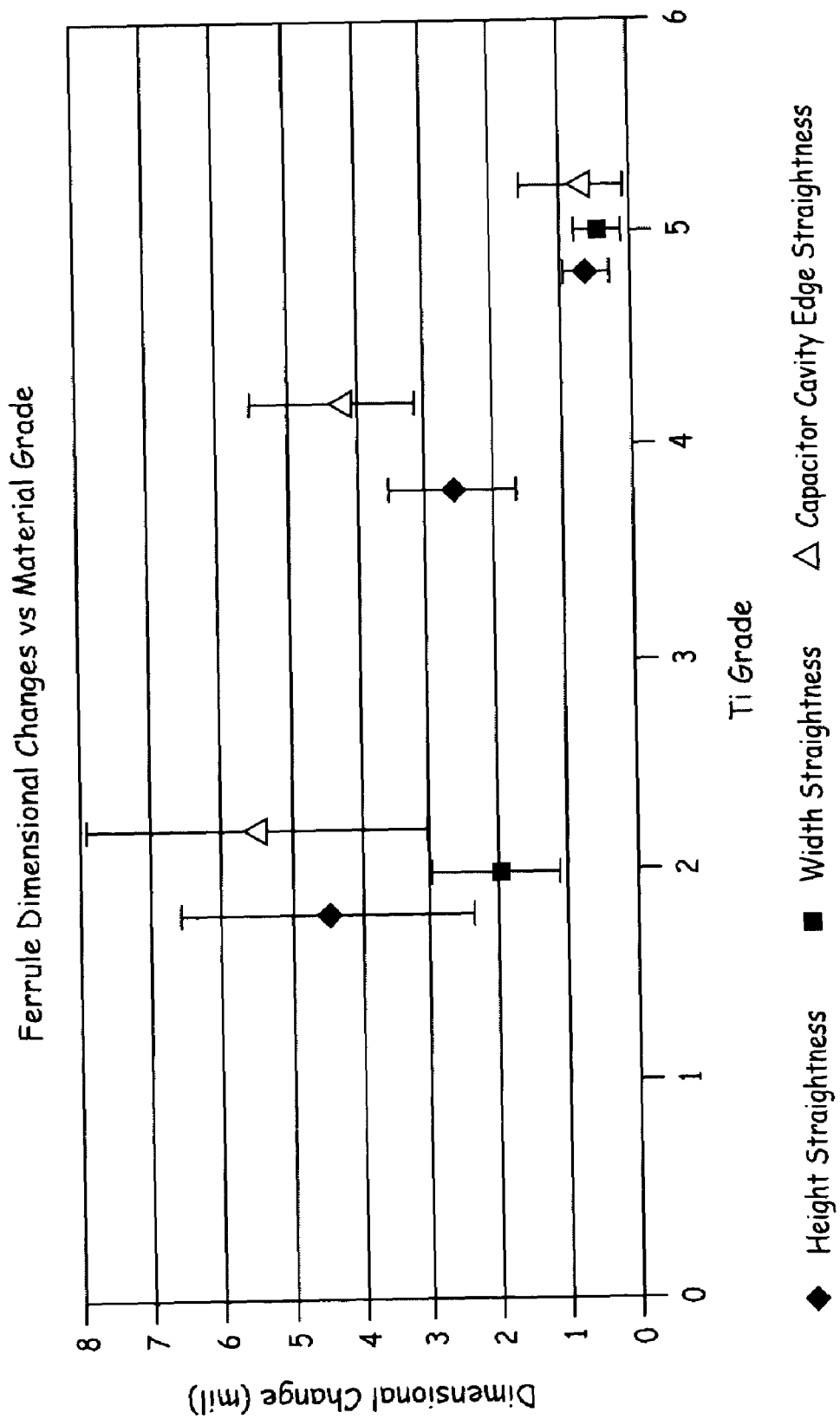
FIG. 2 is a graphical representation of the empirical dimensional data of FIGS. 1A, 1B, and 1C wherein the "height straightness," "width straightness," and "cap cavity straightness" dimensions (and standard deviations for each) as set forth in the table of FIG. 1A for an eight-hole ferrule.

Referring now to FIG. 1A, which provides a table of empirical comparative dimensional data for grade 2 titanium (10), grade 4 titanium (12), and grade 5 titanium (14) ferrules. The departure from a desired dimension is compared in FIG. 1; namely, ferrule features 15: height straightness 16, width straightness 18 and capacitor cavity edge straightness 20. For each of the three grades of titanium the mean and standard deviation values are presented as well as the most likely negative impact of a departure from the desired dimension(s) 21. As will be apparent with reference to the rest of the disclosure herein, the inability to maintain the desired dimension(s) can unfortunately adversely affect the shield (i.e., IMD enclosure) laser welding procedures 22, EMA attachment procedures and EMI filter capacitor containment 24, among others. FIG. 1B depicts an elevational side view of an eight-hole ferrule 100 that illustrates the height straightness dimension 16, and FIG. 1C depicts a plan view of the eight-hole ferrule 100 of FIG. 1B illustrating the width straightness 18 and capacitor cavity (edge) straightness 20 dimensions set forth in the table of FIG. 1A.

FIG. 2 is a graphical representation of the empirical dimensional data of FIGS. 1A, 1B, and 1C wherein the height straightness 16, width straightness 18, and capacitor cavity (edge) straightness 20 dimensions (and standard deviations for each) as set forth in the table of FIG. 1A for the exemplary eight-hole ferrule 100. While the ferrule 100 depicted in FIG. 1B and FIG. 1C has a series of bores 102, greater or fewer such bores 102 may populate the ferrule 100. In addition while the ferrule 100 is depicted as an elongated member having a linear array of bores 102, both the ferrule 100 and the bores 102 can be shaped into any convenient configuration, such as a geometric and/or irregular shape. Further, while the bores 102 are depicted as substantially circular apertures, the bores 102 can also be formed into any convenient configuration. Also, while not depicted in FIG. 1B or FIG. 1C, the conductive elements (104, 106, 108 in other FIGS.) can comprise substantially linear elongated metallic members, elongated serpentine conductive members, sealed braided wire conductors, and the like. Thus, although the description refers primarily to pin-type conductors, the invention is not to be construed as limited to only pin-type conductors.

FIGS. 3A, 3B, 3C, and 3D depict a perspective view of a multi-polar, 9-pin feedthrough array 120 according to the invention wherein eight (104) of the nine pins (104, 108) are capacitively filtered by capacitive coupling circuitry 116 and one pin 108 is not filtered; a plan view of said array 120, and a pair of cross sectional views of said array 120 along lines A—A and B—B, respectively. In addition, a reference ground pin 106 mechanically couples to a portion of the ferrule 100 as is known in the art. An air gap 103 surrounds the pins 104 within the passive capacitor circuitry 116, which can comprise discoidal capacitor elements as are known in the art. The air gap between 103 & 104 is filled with a conductive epoxy, polymide, solder & alike to make electrical connection between pins and the capacitor. Surrounding the pins 104, 108 at their junction with apertures formed in the ferrule 100 an electrically insulative material 114 ensures that the pins 104, 108 are hermetically sealed to the ferrule 100 to prevent ingress of body fluid or debris into the interior of the associated IMD. The insulative material 114 can comprise any known insulator or potting compound or the like, including: a polysilicon material, a glass material, an amorphous material, a ceramic material. In addition, a layer of relatively high temperature brazing alloy 115 is deposited on top of the insulative material 114 as additional barrier to ingress of body fluid and the like in to the IMD. Note that a brazing material also joins the insulator material 114 to the ferrule at the "black squares" located along side each insulator presented in FIG. 3C such that 360° of each insulator is hermetically joined to ferrule member (100) by the braze material. The brazing alloy 115 can comprise gold and/or braze alloy as is known and used in the art. Because use of gold as the brazing material causes the ferrule 100 to reach and/or exceed its characteristic phase transition temperature (approximately 850 degrees Celsius) the inventors posit that grade 4 or grade 5 titanium performs in a surprisingly superior manner than grade 2 titanium (which forms the exterior surface of most IMDs). That is, the inventors suggest that the less pure forms of titanium, such as grade 4 titanium and grade 5 titanium possess greater abundance of minute impurities. The impurities tend to pin to the metallic grains and thereby provide a restraining force to large exaggerated grain growth, during thermal cycles of the ferrule 100 (especially during brazing procedures). The large relative size of the multi-polar ferrule 100 of the invention (compared to the reduced overall size of contemporary IMDs), has exaggerated the difference in the highly pure and less pure grades of titanium. The present invention takes advantage of this surprising property of the higher impurity content grades of titanium to the benefit of many, many IMD patients.

Figure 3:
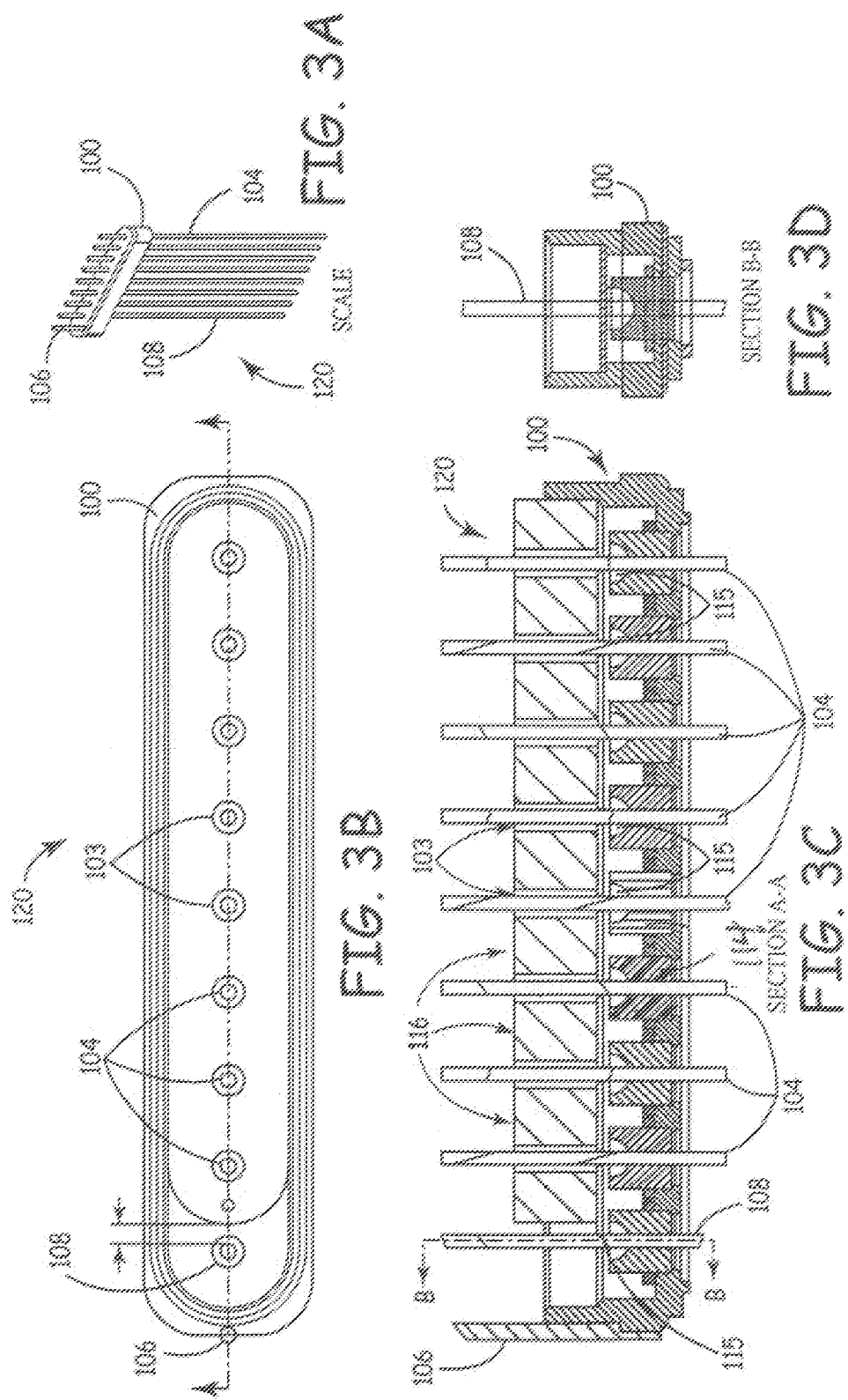
FIGS. 3A, 3B, 3C, and 3D depict a perspective view of a multi-polar, 9-pin feedthrough array according to the invention wherein eight of the pins are capacitively filtered and one pin is not filtered; a plan view of said array, and a pair of cross sectional views of said array, respectively.
Figure 4:
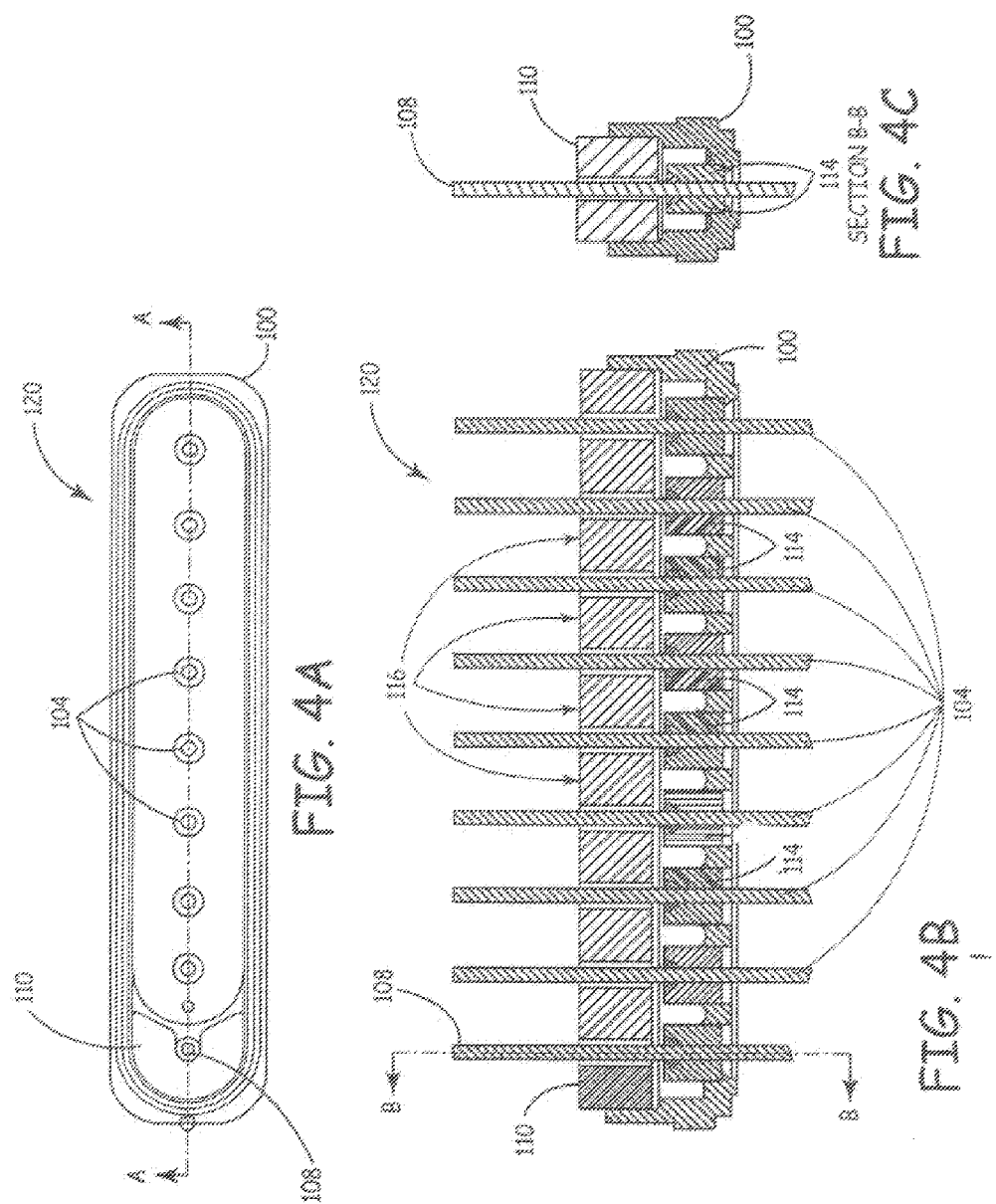
FIGS. 4A, 4B, and 4C depict a plan view of the array of FIG. 3A, and a pair of cross sectional views of said array, respectively, wherein a spacer member is included in proximity to the one unfiltered pin of the array.

FIGS. 4A, 4B, and 4C depict a plan view of the array 120 of FIG. 3A, and a pair of cross sectional views of said array 120 along lines A—A and B—B, respectively, wherein a spacer member 110 is included in proximity to the one unfiltered pin 108 of the array 120. The spacer member 110 provides mechanical support for the pin 108 and is used, at least in part, due to the fact that the size of the capacitor array 116 essentially renders pin 108 recessed relative to pins 104. The spacer member 110 can be fabricated out of any suitable material. For example, any electrically insulative material, such as: a polysilicon material, a glass material, an amorphous material, a ceramic material, polymer-based material and the like. In the event that electrically conductive material is employed, at least the interior portion proximate the pin 108 ought to be covered with a suitable dielectric/insulating material. This could be in the form of a polymer sleeve-tube structure or surrounding pin 108 with a nonconductive material. If the spacer is made of a conducting material the spacer is electrically conducted to the ferrule via the ground terminal of the adjacent capacitor forming a coaxially shielded structure about pin 108. The insulator members 114 are shown in FIG. 4B surrounding each of the pins 104, 108 providing a hermetic seal therearound.

Figure 5:
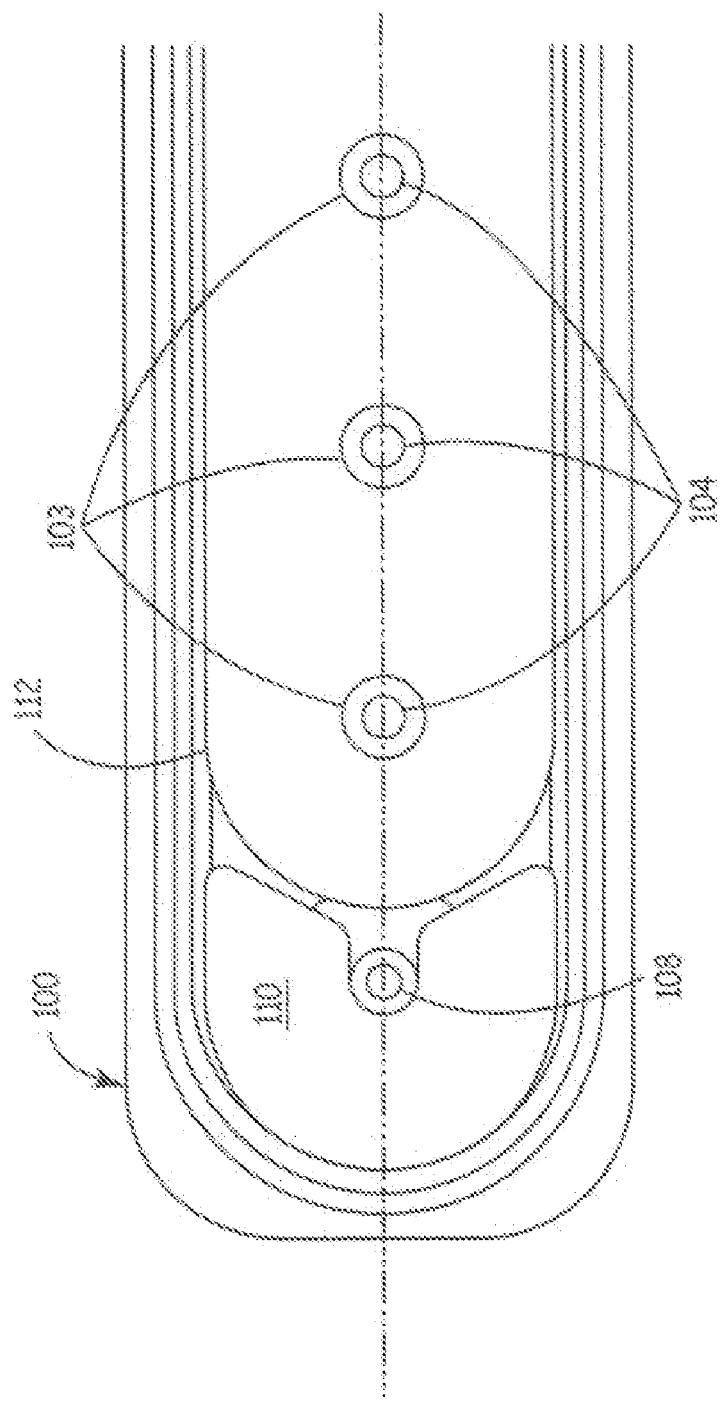
FIGS. 5, 6, and 7 are enlarged plan view depicting alternative embodiments of a few spacer members for use according to the present invention.
Figure 6:
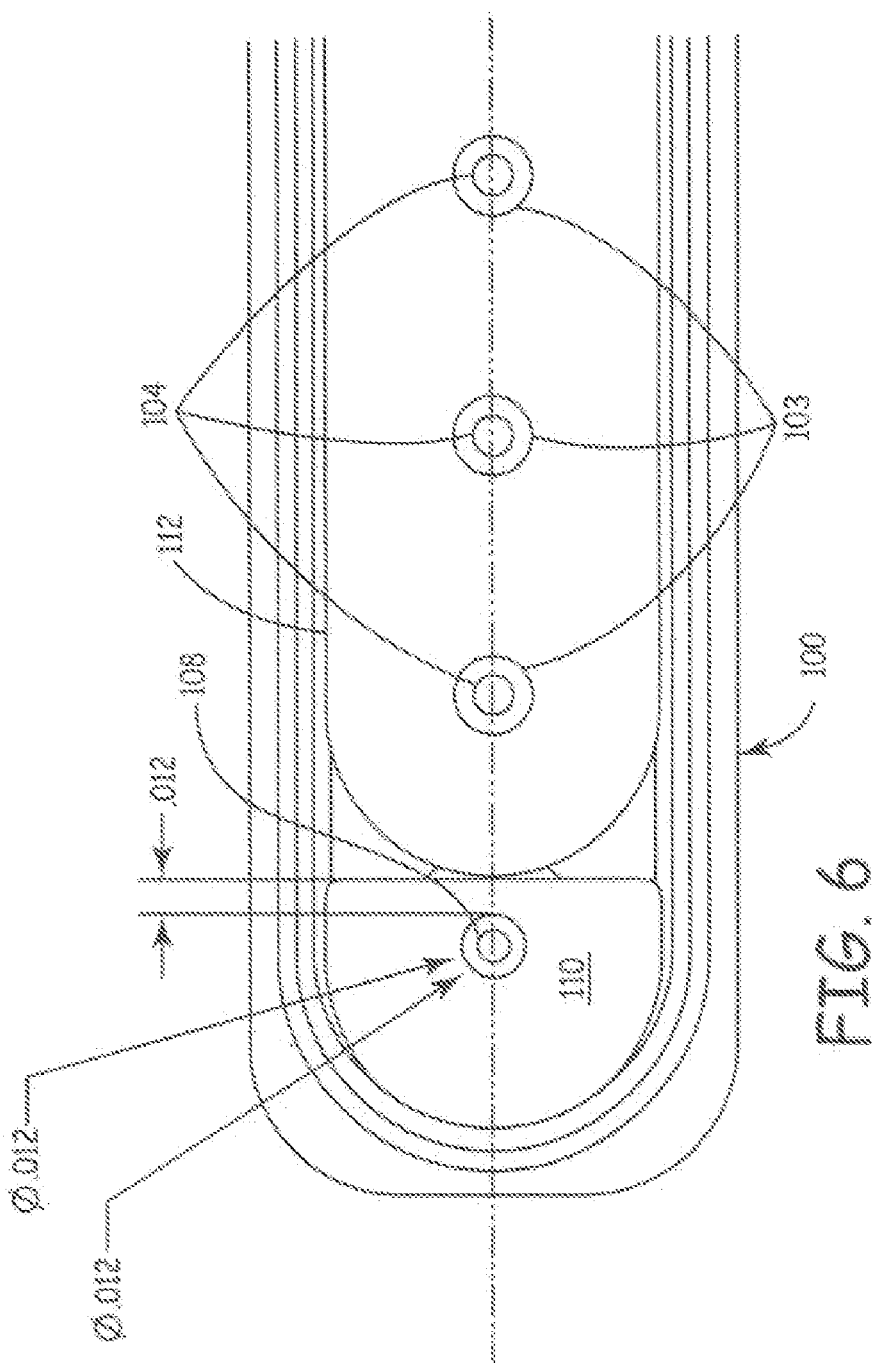
Figure 7:
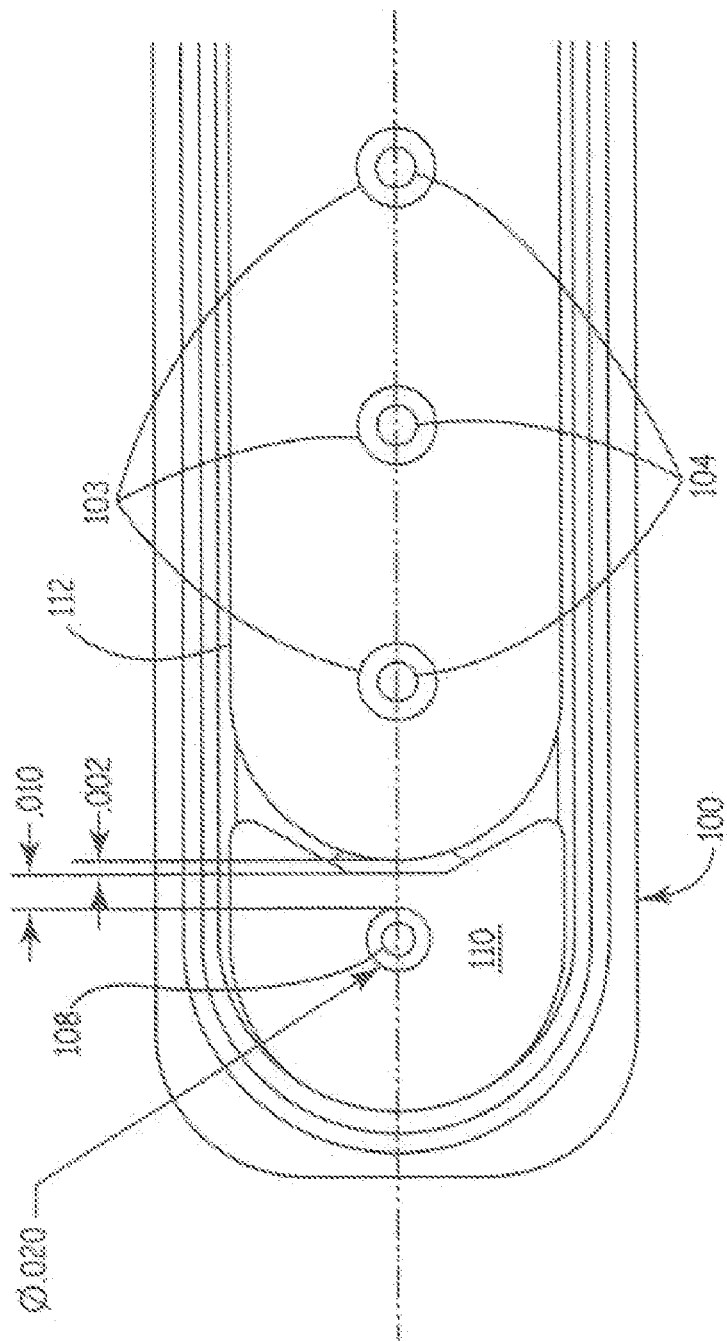
Figure 8A:
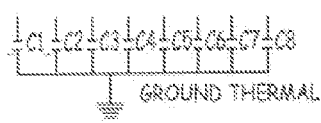
FIGS. 8A, 8B, 8C, and 8D depict a 9-hole capacitor array schematically, in a perspective view, in a plan view, and in an elevational cross-sectional view, respectively.
Figure 8B:
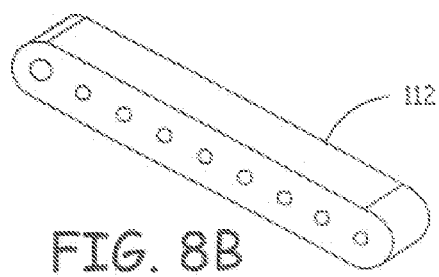
Figure 8C:
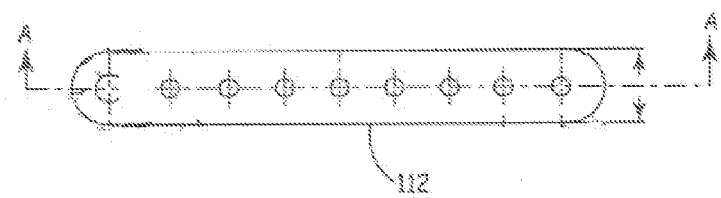
Figure 8D:
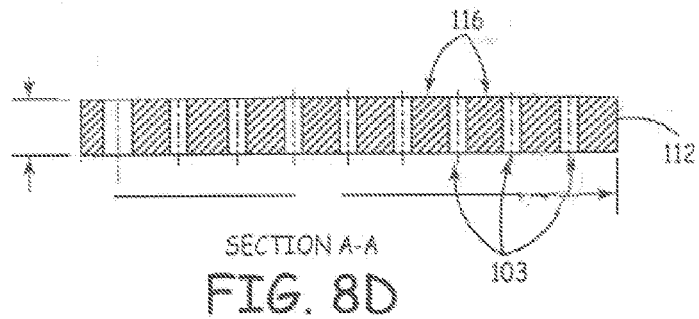

FIGS. 5, 6, and 7 are enlarged plan view depicting alternative embodiments of a few different configurations for the spacer member 110 for use with multi-polar arrays 120 according to the present invention. In FIG. 5 the spacer member 110 has a slot feature formed in one side so that the spacer member 110 can be simply and easily placed into position proximate pin 108. In FIG. 6 the spacer member 110 is a generally D-shaped member having a pin-admitting bore formed therein. In this embodiment the spacer member 110 can optionally abut the capacitor array 112. In FIG. 7, the spacer member 110 is shaped to correspond to the interior geometry of the ferrule 100 and the capacitor array 112 such that the side proximate the array 112 has two relatively long radius corners defining three surfaces that approximate the adjacent side of the array 122. In this embodiment, the spacer member 110 has a pin-admitting bore formed therein.

FIGS. 8A, 8B, 8C, and 8D depict a 9-hole capacitor with 8 functioning capacitor terminals (holes) array 112 schematically, in a perspective view, in a plan view, and in an elevational cross-sectional view along lines A—A, respectively. In the array 112 depicted the hole for pin 108 is larger than the holes 103 for the pins 104 (not shown) and the discrete capacitive elements 116 surrounding the holes 103 do not surround the relatively large hole for pin 108. Size of hole containing the unfiltered pin (pin 108 of FIG. 4) is larger than the rest of the holes in the capacitor serves to increase the separation gap between the capacitor wall and the pin to reduce capacitive coupling to the pin.

The present invention has been described with reference to a few discrete embodiments but is not to be construed as so limited. As those of skill in the art appreciate the various components of the invention can be substituted or modified slightly without departing from the scope of the invention herein disclosed. Indeed, the invention is defined by the appended claims which define the true metes and bounds thereof, as well as equivalents thereof.

The invention claimed is:

1. A multi-polar array for an implantable medical device, comprising;
   a titanium ferrule surrounding the outer periphery of the array and adapted to mechanically couple to a corresponding inner periphery of a titanium surface of an implantable medical device, said ferrule having a plurality of conductive pin-receiving bores formed through a major surface thereof, and wherein said ferrule consists of one of grade 4 titanium and grade 5 titanium;
   a plurality of electrically insulative members sealingly disposed within each said plurality of bores and wherein each of said members is adapted to receive at least one conductive feedthrough pin;
   a plurality of conductive feedthrough pins, each said pin disposed within one of said plurality of electrically insulative members; and
   a plurality of capacitive elements adapted to reduce or eliminate electromagnetic interference from at least some of the plurality of the conductive feedthrough pins, effectively disposed proximate said at some of the plurality of the conductive feedthrough pins
   wherein the plurality of conductive feedthrough pins exceeds the plurality of capacitive elements by at least one pin, so that an analog and/or digital signal coupled to a non-capacitively filtered feedthrough pin substantially completely conducts via said pin.

2. A multi-polar array according to claim 1, wherein the plurality of pin-receiving bores comprises at least four bores.

3. A multi-polar array according to claim 1, wherein the plurality of pin-receiving bores comprises at least six bores.

4. A multi-polar array according to claim 1, wherein the plurality of pin-receiving bores comprises at least eight bores.

5. A multi-polar array according to claim 4, wherein the plurality of pin-receiving bores are arranged in a linear array of bores.

6. A multi-polar array according to claim 1, wherein the titanium surface consists of grade 2 titanium.

7. A multi-polar array according to claim 1, wherein the plurality of electrically insulative members comprises at least one of: a polysilicon material, a glass material, an amorphous material, a ceramic material.

8. A multi-polar array according to claim 1, wherein at least one of the plurality of conductive feedthrough pins comprises one of: a titanium material, a tantalum material, a niobium material, a platinum material, or an alloy of any foregoing materials.

9. A multi-polar array according to claim 1, further comprising a spacer element disposed proximate the non-capacitively filtered feedthrough pin.

10. A multi-polar array according to claim 9, wherein said spacer element includes a feature abutting a portion of the non-capacitively filtered feedthrough pin, said feature comprising one of: a bore, a slot, an edge surface, a wedge-shaped cut-out.

11. A multi-polar array according to claim 9, wherein said spacer element comprises at least one of: a resin-based material, a polymer-based material, an alumina material, a polysilicon material, a glass material, an amorphous material, a ceramic material.

12. A multi-polar array according to claim 1, wherein the non-capacitively filtered feedthrough pin is electrically coupled to operative circuitry of the implantable medical device.

13. A multi-polar array according to claim 1, further comprising:
   an active electrical circuit coupled to at least one of said plurality of conductive feedthrough pins.

* * * * *